United States Patent
Patterson et al.

(10) Patent No.: US 9,664,699 B2
(45) Date of Patent: May 30, 2017

(54) COLORIMETRIC DETERMINATION OF THE TOTAL OIL CONTENT OF A PLANT TISSUE SAMPLE USING ALKALINE SAPONIFICATION

(71) Applicant: Dow AgroSciences LLC, Indianapolis, IN (US)

(72) Inventors: Thomas G. Patterson, Westfield, IN (US); Ted Freeman, Shelbyville, IN (US); Joshua A. Flook, Tipton, IN (US)

(73) Assignee: Dow AgroSciences LLC, Indianapolis, IN (US)

(*) Notice: Subject to any disclaimer, the term of this patent is extended or adjusted under 35 U.S.C. 154(b) by 0 days.

(21) Appl. No.: 15/164,727

(22) Filed: May 25, 2016

(65) Prior Publication Data

US 2016/0291044 A1    Oct. 6, 2016

Related U.S. Application Data

(62) Division of application No. 13/687,898, filed on Nov. 28, 2012, now Pat. No. 9,395,377.

(60) Provisional application No. 61/581,552, filed on Dec. 29, 2011.

(51) Int. Cl.
*G01N 33/92* (2006.01)
*A01H 1/02* (2006.01)

(52) U.S. Cl.
CPC .............. *G01N 33/92* (2013.01); *A01H 1/02* (2013.01)

(58) Field of Classification Search
None
See application file for complete search history.

(56) References Cited

U.S. PATENT DOCUMENTS

| 4,241,178 | A  | 12/1980 | Esders et al. |
| 6,770,801 | B2 | 8/2004  | Leto et al. |
| 6,809,819 | B1 | 10/2004 | Vinjamoori |
| 2004/0036022 | A1 | 2/2004 | Gore et al. |
| 2006/0112628 | A1 | 6/2006 | Kotyk et al. |

FOREIGN PATENT DOCUMENTS

| KR | 1020100136978 | 12/2010 |
| WO | 2009107820 | 9/2009 |
| WO | 2010142424 | 12/2010 |

OTHER PUBLICATIONS

McGowan et al. (Clin. Chem. 29/3, pp. 538-542 (1983)).*
Conkey et al. (IPC Technical Paper Series; No. 316, pp. 1-5 (1988)).*
Vaknin et al. (Industrial Crops and Products 34, pp. 1029-1034 (2011)).*

(Continued)

*Primary Examiner* — Brent Page
*Assistant Examiner* — Jared Shapiro
(74) *Attorney, Agent, or Firm* — Eric J. Kraus; Magleby Cataxinos & Greenwood

(57) ABSTRACT

This disclosure concerns plants, plant materials, and the oil characteristics thereof. In embodiments, compositions and methods for determining the total oil content of plant materials are provided. Such methods and compositions may in some embodiments allow for the characterization and screening of oil traits and sub-traits that are difficult or impossible to distinguish by conventional techniques.

15 Claims, 6 Drawing Sheets

(56) References Cited

OTHER PUBLICATIONS

BioAssay Systems, Triglyceride, ENzyChorm Triglyceride Assay Kit (Catl ETGA-200), 2008, 1 page.
Conkey et al.; Determination of Triglycerides in Plant Tissues; IPC Technical Paper Series; No. 316; Dec. 1988; 7 pages.
International Search Report and Written Opinion for PCT Application No. PCT/US2012/066863, mailed Mar. 13, 2013.
McGowan et al., "A peroxidase-coupled method for the colorimetric determination of serum triglycerides," Clinical Chemistry, 1983, pp. 538-542, vol. 29, No. 3.

\* cited by examiner

COLORIMETRIC DETERMINATION OF THE TOTAL OIL CONTENT OF A PLANT TISSUE SAMPLE USING ALKALINE SAPONIFICATION

CROSS-REFERENCE TO RELATED APPLICATION

This application is a divisional of U.S. patent application Ser. No. 13/687,898 filed Nov. 28, 2012, which claims the benefit of U.S. Provisional Patent Application Ser. No. 61/581,552, filed Dec. 29, 2011, the disclosures of each are hereby incorporated herein in their entirety by this reference.

TECHNICAL FIELD

The present disclosure relates to compositions and methods for analysis of plant oils in a sample.

BACKGROUND

In addition to direct human consumption, vegetable oil has added value for livestock feed, due to its higher energy density and is also increasingly used as a primary source for biodiesel production, particularly in Europe. Vegetable oils with high oleic acid (a monounsaturated fatty acid), and/or low levels of saturate fatty acids, provide considerable health and cooking benefits when compared to saturated and polyunsaturated fatty acids. Kinney et al. (2002) *Biochem. Soc. Trans.* 30:1099-103; White and Weber (2003) "Lipids of the kernel," in *Corn: Chemistry and Technology* 2$^{nd}$ Ed., Vol. 10, Eds. White & Johnson, American Association of Cereal Chemists, Inc., St. Paul, Minn., pp. 355-95.

Though not a typical oil crop, high-oil (HO) corn has attracted considerable attention because corn oil offers high nutritional value for human consumption, and corn meal forms a large proportion of world's animal feed stock. Weber (2003) "Lipids of the kernel," In *Corn: Chemistry and Technology* 2$^{nd}$ Ed., Vol. 10, Eds. White & Johnson, American Association of Cereal Chemists, Inc., St. Paul, Minn., pp. 11-349; Shen et al. (2010) *Plant Physiol.* 153: 980-7. The Illinois High-Oil (IHO) population (Moose et al. (2004) *Trends Plant Sci.* 9:358-64) and the Alexho Single-Kernel (ASK) synthetic population (Lambert et al. (2004) "Single kernel selection for increased grain oil in maize synthetics and high-oil hybrid development," in *Plant Breeding Reviews Part* 1, Vol. 1, Ed. Janick, John Wiley & Sons, Inc., Hoboken, N.J., pp. 153-75) are examples of high-oil maize developed by breeders through recurrent selection. Seed oil content in these populations has reached as high as 22%, and oleic acid contents in both populations are also elevated. Poneleit and Alexander (1965) *Science* 147:1585-6; Zheng et al. (2008) *Nat. Genet.* 40:367-72. Maize varieties with very high oleic acid and/or low saturate fatty acids have also been reported. U.S. Pat. Nos. 6,770,801 and 6,914,176. However, large scale commercial HO maize hybrids have not been released due to significant reductions in grain yield and other undesirable agronomic traits associated with HO germplasm. Nonetheless, these high-oil lines have provided valuable materials for QTL mapping and gene discovery, because long-term selection has accumulated uncommon alleles for oil and fatty acid composition. Recent studies have identified several major oil and fatty acid composition QTLs in these germplasm. Mangolin et al. (2004) *Euphytica* 137:251-9; Dudley et al. (2004) *Crop Sci.* 44:1419-28; Willmot et al. (2006) *Maydica* 51:187-99; Clark et al. (2006) *Crop Sci.* 46:807-19; Beló et al. (2008) *Mol. Genet. Genomics* 279:1-10; Zheng et al. (2008), supra; Wassom et al. (2008) *Crop Sci.* 48:243-52; Wassom et al. (2008) *Crop Sci.* 48:69-78; Yang et al. (2010) *Theor. Appl. Genet.* 120:665-78. Despite a good understanding of the plant oil and fatty acid biosynthetic pathways and a number of QTLs identified, very few genes underlying these QTLs, particularly those for oil QTLs, have been cloned in maize. Zheng et al. (2008), supra; Beló et al. (2008), supra. Most of this can be attributed to the fact that each QTL, even the major ones, only explains a small portion (10% or less) of phenotypic variation and is affected by the environment.

However, another significant reason that few genes underlying oil and fatty acid QTLs in high-oil maize have been identified is that conventional methods for oil measurement are inadequate for determination of oil phenotypes in maize. For example, methods for oil measurement with reasonable throughput are usually whole seed and concentration-based, whereas most of maize seed oil (85-90%) is located in the embryo and determined by the oil concentration of the embryo and the proportion of the seed occupied by the embryo. White and Weber (2003), supra. This discrepancy may sometimes produce misleading oil data because seed oil concentration is also significantly affected by seed and endosperm sizes. Further, the determination of the total oil content of plant tissues is typically based on the gravimetric extraction of oil from tissue using an organic solvent. This technique requires a relatively large amount of tissue to allow an accurate mass determination. Direct measurements using pulsed NMR may also be used, but this technique also requires a large amount of tissue to have sufficient liquid oil for detection.

Thus, despite a need for improved oil phenotype determination in plants (including maize) that has existed at least since the development of high-oil corn, and therefore for more accurate oil measurement techniques that can be conducted using relatively small samples, such techniques have not heretofore been achieved.

DISCLOSURE

Described herein is a novel method for the characterization of oil content in plant materials. Methods of the invention may be used to quantify the total oil content of any type of plant material from any plant (e.g., corn, soya, canola, sunflower, and cotton). In particular embodiments, a method for determining the total oil content in a plant material may be used to determine the oil content in a small sample of plant material. Examples of such small samples include samples in which the oil content is not able to be accurately and efficiently determined by classical techniques (e.g., a single embryo sample).

In particular embodiments, oil is solvent-extracted from a sample comprising dried, ground plant material. The extracted oil may then be saponified using a base (e.g., potassium hydroxide). Glycerol may subsequently be measured using an enzyme triglyceride reagent. The end reaction product may be determined colorimetrically (e.g., spectrophotometrically), and the glycerol concentration in the sample may be calculated from the colorimetric data. The concentration of glycerol in the sample may then be used to calculate the total oil content of the sample.

The foregoing and other features will become more apparent from the following detailed description of several embodiments, which proceeds with reference to the accompanying figures.

DETAILED DESCRIPTION

I. Overview of Several Embodiments

Figure 1:
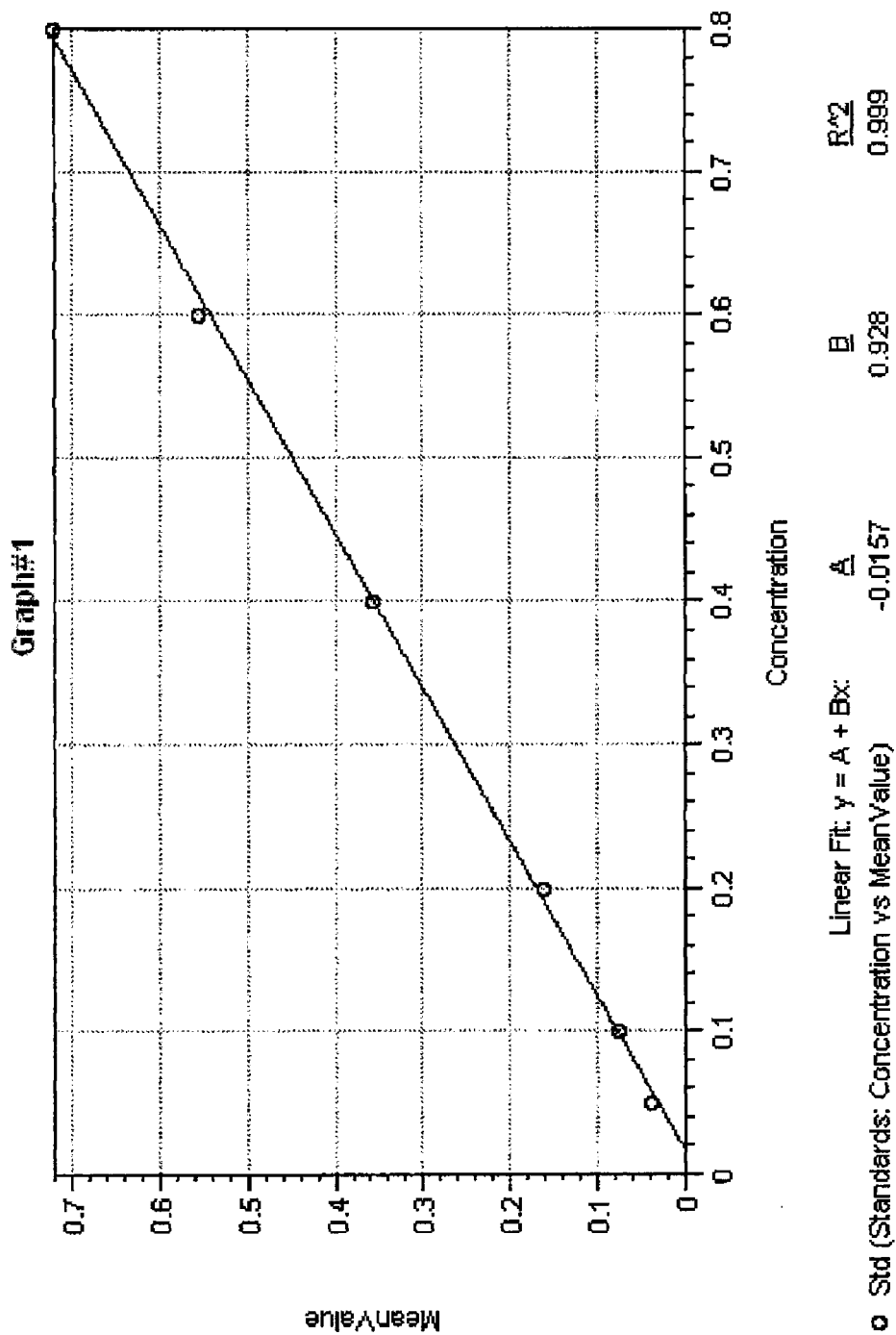
FIG. 1 includes a plot and linear fit of the average absorbance vs. oil standard concentration for each of several concentrations. The absorbance of the "blank" has been subtracted from the data.

Embodiments of the invention provide methods that allow the oil characterization of plant materials (e.g., measurement of total oil content) on a small scale that has been heretofore unachievable using conventional oil measurement techniques. These methods are used in particular embodiments to address urgent problems in plant breeding that have long remained unsolved.

In some examples, a method according to the invention may include a highly sensitive and specific enzymatic colorimetric assay for the detection of glycerol that is coupled to alkaline saponification of oils from a plant material. In particular embodiments, such an assay may allow accurate quantification of the total oil content in any plant material, including, for example, very small tissue samples that are not able to be analyzed by conventional techniques (e.g., a single embryo). Thus, methods provided in some embodiments may allow analysis and screening of previously known, as well as novel, plant varieties for traits and characteristics that may have previously escaped detection.

In some embodiments, alkaline saponification of oils from a plant material is performed in a first step, which step is followed by the colorimetric detection of glycerol produced from the saponification reaction in a subsequent step. In other embodiments that may be particularly suited to high-throughput applications, alkaline saponification of oils from a plant material is performed simultaneously with the colorimetric detection of glycerol produced from the saponification reaction.

II. Abbreviations

4-AAP 4-aminoantipyrine
ASK Alexho Single-Kernel corn
ATP adenosine-5-triphosphate
DAP dihydroxyacetone phosphate
EER Endosperm/Embryo (weight) Ratio
G3P glycerol-3-phosphate
GK glycerol kinase
GPO glycerophosphate oxidase
HO high oil
$H_2O_2$ hydrogen peroxide
IHO Illinois High-Oil corn
QTL quantitative trait locus
RBD refined, bleached, and deodorized
TBHB 3-hydroxy-2,4,6-tribomobenzoic acid

III. Terms

Oil: As used herein, the term "oil" may refer to lipid molecules that comprise a glycerol backbone (e.g., triglycerides, diglycerides, and monoglycerides). Thus, the term "oil" may not include lipid molecules without a glycerol backbone, for example and without limitation: waxes, free fatty acids, and unsaponifiable lipids.

Fatty acids are long chain aliphatic acids (alkanoic acids) of varying chain lengths (e.g., from about C12 to C22, although both longer and shorter chain-length acids are known). The structure of a fatty acid is represented by the notation, $x:y\Delta z$, where "x" is the total number of carbon (C) atoms in the particular fatty acid, and "y" is the number of double bonds in the carbon chain in the position "z," as counted from the carboxyl end of the acid.

Oils that may be isolated or extracted from a plant tissue sample are typically referred to as "vegetable oils." Vegetable oils generally are liquids at room temperature, and are composed primarily of triglycerides. Some embodiments concern "total oils," for example, as may be isolated or extracted from a plant material (e.g., a plant tissue sample). The "total oil" of a plant material is the total quantity of all the glycerol backbone-containing lipid molecules in the plant material. Total oil content may be calculated directly (i.e., by measuring the total oil in a sample), or indirectly (i.e., by measuring the oil in a fraction of the sample, and scaling the amount measured to estimate the total oil in the sample).

The oil content of a seed is typically represented as a percentage of the whole dried seed. Conventional methods for determining oil content include NMR; NIR; and Soxhlet extraction. The percent composition of total fatty acids in seed is typically determined by extracting a sample of oil from seed, producing methyl esters of fatty acids present in the oil sample, and analyzing the proportions of the various fatty acids in the sample using gas chromatography.

Plant material: As used herein, the term "plant material" refers to any processed or unprocessed material derived, in whole or in part, from a plant. For example and without limitation, a plant material may be a plant part, a seed, a fruit, a leaf, a root, a plant tissue, a plant tissue culture, a plant explant, a plant cell, or whole plant. A sample of a plant material may refer to a fraction or portion of the plant material, for example, a fraction or portion to be analyzed by a method according to the invention in order to extrapolate a result for the total plant material from which the sample is obtained. A sample of a plant material may also refer to the plant material itself, if the entire plant material is subjected to analysis.

Saponification: As used herein, the term "saponification" refers to a process that produces a fatty acid salt. Saponification involves the hydrolysis of triglycerides with a base (usually KOH or NaOH) to form the salt of a carboxylate and glycerol. The "saponification value" refers to the amount of base required to saponify a fat sample.

Screening: As used herein, the term "screening" may refer to a procedure used to evaluate a plant material (or a plant from which the plant material was obtained or derived) for a property of interest (e.g., oil content) or trait of interest (e.g., high-oil). A screening procedure is not required to be free of false positives or false negatives, so long as the screening procedure is useful in determining which plant materials have an increased likelihood of comprising the property or trait.

Trait (or phenotype): The terms "trait" and "phenotype" are used interchangeably herein. As used herein, the term "sub-trait" refers to a phenotype that contributes to one or more multivariate traits. For the purposes of the present disclosure, traits of particular interest are plant oil traits (e.g., high oil content, and high embryonic oil content), and sub-traits of particular interest are plant oil sub-traits that contribute to multivariate plant oil traits.

Unless indicated otherwise, the terms "a" and "an" as used herein refer to at least one.

IV. Conversion of Plant Oils into Glycerol via Alkaline Saponification

This disclosure provides methods for the oil characterization of a plant material. In embodiments, oils of the plant material may be saponified by alkaline hydrolysis to stoichiometrically convert the oils into glycerol. Alkaline saponification is non-specific, as the —OH reactant may hydrolyze and/or modify materials in the sample other than the oils. For this reason, the use of bases to saponify triglyceride-containing samples, as opposed to lipase enzymes, is strongly disfavored in diagnostic applications. Further, when alkaline saponification is used for soap making, the triglyceride reactants are typically highly purified from other materials.

Lipids (including vegetable oils, as well as animal fats) may be saponified by alkaline hydrolysis of esters to produce soap (fatty acid salts) and glycerol. The fatty esters in vegetable oil that are hydrolyzed in a saponification reaction include mixtures of triesters called triglycerides, which are derived from diverse fatty acids. Triglycerides may be saponified in either a one- or a two-step process. In a traditional one-step saponification process, the triglycerides are treated with a strong base (e.g., lye), which accelerates cleavage of the ester bond to release the fatty acid salt and glycerol. The resulting soaps may be precipitated from the reaction products by addition of saturated sodium chloride.

Hydrolysis of oils during alkaline saponification occurs via cleavage of the ester bond joining a hydroxyl group of the glycerol backbone with the carboxyl group of an attached fatty acid. The cleavage proceeds by nucleophilic acyl substitution of the base anion. Any base able to perform this hydrolysis reaction in a triglyceride may be used in some embodiments of the invention. In particular embodiments, the base anion is a hydroxide anion, as provided for example, in a salt molecule. Thus, some examples comprise the use of alkali metal salts (e.g., KOH and NaOH) in a saponification reaction to produce glycerol from the constituent fatty acids of vegetable oil. Plant materials and the oils contained therein may be treated (e.g., solvent extracted, such as heptanes extracted) or untreated prior to saponification in particular embodiments.

Though embodiments of the invention concern the oil characteristics of a plant material, which are generally provided by particular fatty acids, the methods described and exemplified herein operate in part by detecting and/or measuring the free glycerol that is released by saponification. Techniques utilizing lipases to cleave serum triglycerides have been developed for diagnostic clinical applications according to the strict demands of those applications. Chemistry and reagents used in such techniques have been adapted to provide a useful technique for the measurement of glycerol from saponified plant materials in some embodiments.

V. Glycerol Detection Assays

Enzymatic colorimetric glycerol detection assays have been developed to measure serum triglyceride levels, as serum triglyceride levels are used in clinical diagnosis of human subjects for hyperlipemia, atherosclerosis, and pacreatitis. See, e.g., U.S. Pat. No. 4,241,178. The progress with regard to these clinical glycerol detection assays has greatly outpaced the progress of oil characterization in plants. In methods employing such clinical assays, triglycerides in a sample are hydrolyzed to glycerol and fatty acids. In order to achieve, for example, complete and selective reaction with triglycerides, as well as accurate clinical measurement, these methods utilize lipase enzymes to perform the hydrolysis step. See, e.g., EnzyChrom™ Triglyceride Assay Kit (BioAssay Systems Cat# ETGA-200); and the triglyceride reagent set available from Pointe Scientific (e.g., Cat# T7531-150).

After hydrolysis and release of glycerol, the glycerol may be detected and measured using glycerol detection reagents, such as, for example and without limitation, a glycerol detection reagent that is commercially available as a component of a lipase-based triglyceride diagnostic kit. In one representative example of such a kit (Pointe Scientific Cat# T7531-150), the glycerol in a sample is phosphorylated by ATP to produce glycerol-3-phosphate (G3P) and adenosine-5-diphosphate in a reaction catalyzed by glycerol kinase (GK). Glycerol-3-phosphate is then converted to dihydroxyacetone phosphate (DAP) and hydrogen peroxide ($H_2O_2$) by glycerophosphate oxidase (GPO). The $H_2O_2$ is reacted with 4-aminoantipyrine (4-AAP) and 3-hydroxy-2,4,6-tribomobenzoic acid (TBHB) in a reaction catalyzed by peroxidase to yield a red-colored quinoneimine dye. In this assay, the intensity of the color produced is directly proportional to the concentration of triglycerides in the original sample when measured at 540 nm.

Other methods for the determination of triglycerides through lipase activity and glycerol detection are described, for example, in Sugiura et al. (1977) *Clin. Chim. Acta* 81(2):125-30, and McGowan et al. (1983) *Clin. Chem.* 29:538. Kits for performing these and other methods are commercially available from several manufacturers, for example and without limitation, BioAssay Systems (Hayward, Calif., USA), Medibena (Vienna, Austria), Diagnostic Chemicals Ltd. (Charlottetown, PE, Canada), and Pointe Scientific.

Reagents for glycerol-based triglyceride detection from any of the foregoing clinical methods and kits may be used in some embodiments of the invention. For example, a Free Glycerol Reagent (available through Sigma Aldrich, Cat# F6428) or a Triglyceride Reagent Set (available through Pointe Scientific, Inc., Cat# T7532-120) may be used. Though the lipase enzyme is a critical and indispensible component of these clinical methods and kits in their intended applications, it will be understood that the lipase enzyme may be separated from the other reagents in the clinical methods and kits when those reagents for use in the presently described methods are obtained from such clinical methods and kits.

In particular embodiments, a glycerol detection reagent is a reagent (or combination of reagents) that may be used to detect a molecule that is present in the sample in a stoichiometric amount with regard to oils in the starting material. Thus, a glycerol detection reagent may not necessarily directly detect glycerol, but may indirectly detect glycerol by directly detecting the product of a stoichiometric reaction (or chain of reactions) that converts glycerol into the product. For example, in the aforementioned exemplary embodiment utilizing the Triglyceride Reagent Set from Pointe Scientific, TBAB and peroxidase are glycerol detection reagents, and these reagent directly detect $H_2O_2$, which is stoichiometrically produced in a series of reactions from glycerol. In this example, $H_2O_2$ is used to produce a colored product (a quinoneimine dye) that may be determined as a reaction end-product in an amount that is stoichiometrically related to the glycerol content of the sample. In some examples, a glycerol detection reagent may detect the molecule, such that the amount of the molecule in the sample can be accurately quantified. Other enzymes and reagents may be used in particular examples to produce a detectable signal that is correlated to the amount of glycerol in the sample (and hence, oil in the starting material), as will be appreciated by those of skill in the art. For example, a variety of reagents may be reacted with hydrogen peroxide produced from glycerol to generate a detectable (e.g., colored) product.

A glycerol detection reagent may also be a reagent (i.e., an enzyme or substrate) that operates in a reaction scheme to produce a reaction product that is stoichiometrically related to the glycerol content in the sample, which reaction product may then be used to produce a colored product that may be determined as a reaction end-product in an amount that is stoichiometrically related to the glycerol content of the sample. Such a reaction scheme may comprise one or more distinct chemical reactions. For example, in the aforementioned exemplary embodiment utilizing the Triglyceride Reagent Set from Pointe Scientific, ATP and GK are glycerol detection reagents that are used in a first distinct chemical reaction to produce G3P, which is stoichiometrically related to the glycerol content of the sample. GPO is a further glycerol detection reagent that is used in a second distinct chemical reaction to produce $H_2O_2$, which is stoichiometrically related to the glycerol content of the sample.

Some embodiments may include an oil standard (e.g., a RBD oil standard) with a known oil content that may be used to calibrate the assay and aid in interpretation of results. In some examples, the oil standard may be from the same plant source as the plant material or sample to be characterized via the method (i.e., soybean oil for soybeans, canola oil for canola, corn oil for corn, etc.). An exemplary oil standard that may be useful in some embodiments may be prepared by: (1) Weighing a sample of the oil (e.g., 1 gram); (2) diluting the oil with a solvent (e.g., heptanes) to a final concentration of, for example, 100 mg/mL; and (3) transferring to a container (e.g., a screw-cap test tube) for storage. Quality control samples may be prepared, as necessary, from a separate weighing of the oil standard, or from a free glycerol standard (e.g., as may be provided with a commercially available glycerol detection reagent, such as the glycerol standard that is provided with the Free Glycerol Reagent from Sigma Aldrich).

Other materials and reagents that may be included in methods according to particular embodiments include buffer(s), surfactant(s), stabilizer(s), filler(s), preservative(s) (e.g., sodium azide), and solvent(s) (e.g., methanol, heptanes). Appropriate signal detection equipment (spectrophotometer, plate reader, etc.), depending upon the reagent and sample volume used, may be selected according to the discretion of the practitioner.

In embodiments, a plant material sample or oil sample from a plant material that is saponified is reacted with a glycerol detection reagent to detect and/or measure the oil content of the sample, in order to determine the presence or absence of an oil trait or sub-trait of interest in the plant from which the sample was obtained. Information thus obtained may be used to evaluate and carry out plant breeding or plant production strategies to introduce and/or maintain the trait or sub-trait of interest in a plant. The exquisite sensitivity and small sample sizes obtainable by methods according to embodiments of the invention allows detection of previously unknown (or difficult to characterize) oil traits and sub-traits, and/or the characterization of oil traits and sub-traits at a previously unachievable level of detail.

VI. Screening, Selective Breeding, and/or Production of a Plant with an Oil Trait Disclosed herein are methods for employing a highly sensitive and specific enzymatic and colorimetric assay to determine the oil characteristics of a plant-based sample, to identify a plant having a particular oil trait or sub-trait. Myriad processes in the art require the identification (and optionally the subsequent selection) of a plant having a particular trait. For example, when a number of plant(s) are suspected of containing a plant with a particular oil trait, it may be desirable to screen those plant(s) to identify a plant with the trait. A number of plants suspected of containing a plant with a particular oil trait may be generated in a plant breeding process, either for the oil trait, or for another trait where the presence of the oil trait in the generated plants is tracked or determined. Such a number of plant(s) may also be generated during the production of a transgenic or genetically modified plant, for example, by using recombinant DNA technology. In these and other applications, it may be desirable to screen plants for a particular oil trait (e.g., an oil trait of interest). Plant materials may be obtained from such plants, and samples of the plant materials thus obtained may be subjected to an assay according to some embodiments of the invention, to identify one or more source plant(s) having the particular oil trait.

A plant-based sample may be prepared from any plant material. The source of a plant-based sample for use in some embodiments may be selected in view of the particular oil trait to be assayed. For example, if the particular oil characteristics of seed oil are assayed, then it may be desirable that the plant-based sample be prepared from seed of the subject plant. In some embodiments, a plant-based sample is prepared from a plant material that is too small for individual analysis of oil characteristics according to conventional methods. Analysis of such individual samples is made possible by methods according to these embodiments, which may lead to the detection of sub-traits or characteristics (e.g., individual sample variability) that may have been previously masked by combination into bulk samples necessary for conventional methods.

Thus, methods according to some embodiments may be used as part of a plant breeding program. For example, progeny plants of a parental cross may be screened for desirable oil traits and/or characteristics, and those progeny plants identified by the screening may be selected for further propagation, e.g., to produce inbred plants comprising the desirable oil trait or characteristic, and/or to introgress the desirable oil trait or characteristic into a particular germplasm.

Methods according to some embodiments may be used as part of a transgenic plant production program. For example, a mapping population of plants may be screened for a desirable oil trait or sub-trait using a method according to some embodiments, and the results of the screen may be used to identify one or more gene(s) that contribute to the oil trait or sub-trait. Once the gene(s) is/are identified, the allele corresponding to the trait or sub-trait may be introduced into a plant, for example, by genetic transformation to produce a genetically modified plant. Additionally or alternatively, a method according to some embodiments may be used to screen plants produced by introducing a gene that contributes to an oil trait or sub-trait of interest (e.g., putative transformants) for the trait or sub-trait, and select plants having the trait or sub-trait. Thus, methods of some embodiments may be used in a program with recombinant genetic techniques to produce inbred plants comprising an oil trait or sub-trait of interest, and/or to introgress the oil trait or sub-trait into a particular germplasm.

In embodiments, once a method as provided herein is used to screen plants and identify those with an oil trait or sub-trait of interest, the oil trait or sub-trait may be transferred into other varieties of the same species of plant, or into another plant, by methods known to those of skill in the art, such as for example and without limitation, conventional plant breeding techniques involving cross-pollination and selection of progeny, wherein the germplasm of the screened and identified plant is incorporated into the other variety or other plant; and genetic transformation.

Thus, an oil trait or sub-trait of interest that is able to be identified by methods according to some embodiments may be combined with other plant traits of interest by transferring the oil trait or sub-trait of interest into a variety or plant comprising the other plant trait of interest. The process of introducing an oil trait or sub-trait of interest into a plant comprising one or more other desirable traits is often referred to as "stacking" of these traits. In some examples, stacking of the oil trait or sub-trait of interest with a plurality of desirable traits may result in further changes or improvements to the oil content or characteristics of the plant. In some examples, stacking of the oil trait or sub-trait of interest with a plurality of desirable traits may result in a plant having the oil trait or sub-trait of interest in addition to one or more (e.g., all) of the plurality of desirable traits.

Examples of traits that may be desirable for combination with an oil trait or sub-trait include, for example and without limitation: plant disease resistance genes (see, e.g., Jones et al. (1994) *Science* 266:789 (tomato Cf-9 gene for resistance to *Cladosporium fulvum*); Martin et al. (1993) *Science* 262:1432 (tomato Pto gene for resistance to *Pseudomonas syringae*); and Mindrinos et al. (1994) *Cell* 78:1089 (RSP2 gene for resistance to *Pseudomonas syringae*)); a gene conferring resistance to a pest; a *Bacillus thuringiensis* protein, a derivative thereof, or a synthetic polypeptide modeled thereon (see, e.g., Geiser et al. (1986) *Gene* 48:109 (Bt δ-endotoxin gene; DNA molecules encoding δ-endotoxin genes can be purchased from American Type Culture Collection (Manassas, Va.), for example, under ATCC Accession Nos. 40098; 67136; 31995; and 31998)); a lectin (see, for example, Van Damme et al. (1994) *Plant Molec. Biol.* 24:25 (*Clivia miniata* mannose-binding lectin genes)); a vitamin-binding protein, e.g., avidin (see International PCT Publication US93/06487 (use of avidin and avidin homologues as larvicides against insect pests)); an enzyme inhibitor; a protease or proteinase inhibitor (see, e.g., Abe et al. (1987) *J. Biol. Chem.* 262:16793 (rice cysteine proteinase inhibitor); Huub et al. (1993) *Plant Molec. Biol.* 21:985 (tobacco proteinase inhibitor I; and U.S. Pat. No. 5,494,813); an amylase inhibitor (see Sumitani et al. (1993) *Biosci. Biotech. Biochem.* 57:1243 (*Streptomyces nitrosporeus* alpha-amylase inhibitor)); an insect-specific hormone or pheromone, e.g., an ecdysteroid or juvenile hormone, a variant thereof, a mimetic based thereon, or an antagonist or agonist thereof (see, e.g., Hammock et al. (1990) *Nature* 344:458 (inactivator of juvenile hormone)); an insect-specific peptide or neuropeptide that disrupts the physiology of the affected pest (see, e.g., Regan (1994) *J. Biol. Chem.* 269:9 (insect diuretic hormone receptor); Pratt et al. (1989) *Biochem. Biophys. Res. Comm.* 163:1243 (allostatin from *Diploptera puntata*); U.S. Pat. No. 5,266,317 (insect-specific, paralytic neurotoxins)); an insect-specific venom produced in nature by a snake, a wasp, or other organism (see, e.g., Pang et al. (1992) *Gene* 116:165 (a scorpion insectotoxic peptide)); an enzyme responsible for a hyperaccumulation of a monoterpene, a sesquiterpene, a steroid, hydroxamic acid, a phenylpropanoid derivative or another non-protein molecule with insecticidal activity; an enzyme involved in the modification, including the post-translational modification, of a biologically active molecule, e.g., a glycolytic enzyme; a proteolytic enzyme; a lipolytic enzyme; a nuclease; a cyclase; a transaminase; an esterase; a hydrolase; a phosphatase; a kinase; a phosphorylase; a polymerase; an elastase; a chitinase; or a glucanase, whether natural or synthetic (see International PCT Publication WO 93/02197 (a callase gene); DNA molecules which contain chitinase-encoding sequences (for example, from the ATCC, under Accession Nos. 39637 and 67152); Kramer et al. (1993) *Insect Biochem. Molec. Biol.* 23:691 (tobacco hornworm chitinase); and Kawalleck et al. (1993) *Plant Molec. Biol.* 21:673 (parsley ubi4-2 polyubiquitin gene); a molecule that stimulates signal transduction (see, e.g., Botella et al. (1994) *Plant Molec. Biol.* 24:757 (calmodulin); and Griess et al. (1994) *Plant Physiol.* 104:1467 (maize calmodulin); a hydrophobic moment peptide (see, e.g., International PCT Publication WO 95/16776 (peptide derivatives of Tachyplesin which inhibit fungal plant pathogens); and International PCT Publication WO 95/18855 (synthetic antimicrobial peptides that confer disease resistance)); a membrane permease, a channel former, or a channel blocker (see, e.g., Jaynes et al. (1993) *Plant Sci.* 89:43 (a cecropin-β lytic peptide analog to render transgenic plants resistant to *Pseudomonas solanacearum*); a viral-invasive protein or a complex toxin derived therefrom (see, e.g., Beachy et al. (1990) *Ann. Rev. Phytopathol.* 28:451 (coat protein-mediated resistance against alfalfa mosaic virus, cucumber mosaic virus, tobacco streak virus, potato virus X, potato virus Y, tobacco etch virus, tobacco rattle virus and tobacco mosaic virus)); an insect-specific antibody or an immunotoxin derived therefrom (see, e.g., Taylor et al., Abstract #497, Seventh Int'l Symposium on Molecular Plant-Microbe Interactions (Edinburgh, Scotland) (1994) (enzymatic inactivation via production of single-chain antibody fragments); a virus-specific antibody (see, e.g., Tavladoraki et al. (1993) *Nature* 366:469 (recombinant antibody genes for protection from virus attack)); a developmental-arrestive protein produced in nature by a pathogen or a parasite (see, e.g., Lamb et al. (1992) *Bio/Technology* 10:1436 (fungal endo α-1,4-D-polygalacturonases facilitate fungal colonization and plant nutrient release by solubilizing plant cell wall homo-α-1,4-D-galacturonase; Toubart et al. (1992) *Plant J.* 2:367 (endopolygalacturonase-inhibiting protein)); and a developmental-arrestive protein produced in nature by a plant (see, e.g., Logemann et al. (1992) *Bio/Technology* 10:305 (barley ribosome-inactivating gene providing increased resistance to fungal disease)).

Further examples of traits that may be desirable for combination with an oil trait or sub-trait include, for example and without limitation: genes that confer resistance to a herbicide (Lee et al. (1988) *EMBO J.* 7:1241 (mutant ALS enzyme); Miki et al. (1990) *Theor. Appl. Genet.* 80:449 (mutant AHAS enzyme); U.S. Pat. Nos. 4,940,835 and 6,248,876 (mutant 5-enolpyruvylshikimate-3-phosphate synthase (EPSPs) genes providing glyphosate resistance); U.S. Pat. No. 4,769,061 and ATCC accession number 39256 (aroA genes); glyphosate acetyl transferase genes (glyphosate resistance); other phosphono compounds from *Streptomyces* species, including *Streptomyces hygroscopicus* and *Streptomyces viridichromogenes*) such as those described in European application No. 0 242 246 and DeGreef et al.

(1989) *Bio/Technology* 7:61 (glufosinate phosphinothricin acetyl transferase (PAT) genes providing glyphosate resistance); pyridinoxy or phenoxy proprionic acids and cyclohexones (glyphosate resistance); European patent application No. 0 333 033 and U.S. Pat. No. 4,975,374 (glutamine synthetase genes providing resistance to herbicides such as L-phosphinothricin); Marshall et al. (1992) *Theor. Appl. Genet.* 83:435 (Acc1-S1, Acc1-S2, and Acc1-S3 genes providing resistance to phenoxy proprionic acids and cyclohexones, such as sethoxydim and haloxyfop); WO 2005012515 (GAT genes providing glyphosate resistance); WO 2005107437 (Genes conferring resistance to 2,4-D, fop and pyridyloxy auxin herbicides); and an herbicide that inhibits photosynthesis, such as a triazine (psbA and gs+ genes) or a benzonitrile (nitrilase gene) (see, e.g., Przibila et al. (1991) *Plant Cell* 3:169 (mutant psbA genes); nucleotide sequences for nitrilase genes are disclosed in U.S. Pat. No. 4,810,648, and DNA molecules containing these genes are available under ATCC Accession Nos. 53435, 67441, and 67442; and Hayes et al. (1992) *Biochem. J.* 285:173 (glutathione S-transferase)).

Further examples of traits that may be desirable for combination with an oil trait or sub-trait include, for example and without limitation, genes that confer or contribute to a value-added trait, for example, modified fatty acid metabolism (see, e.g., Knultzon et al. (1992) *Proc. Natl. Acad. Sci. U.S.A.* 89:2624 (an antisense gene of stearyl-ACP desaturase to increase stearic acid content of the plant)); decreased phytate content (see, e.g., Van Hartingsveldt et al. (1993) *Gene* 127:87 (an *Aspergillus niger* phytase gene enhances breakdown of phytate, adding more free phosphate to the transformed plant); and Raboy et al. (1990) *Maydica* 35:383 (cloning and reintroduction of DNA associated with an allele responsible for maize mutants having low levels of phytic acid)); and modified carbohydrate composition effected, for example, by transforming plants with a gene coding for an enzyme that alters the branching pattern of starch (see, e.g., Shiroza et al. (1988) *J. Bacteriol.* 170:810 (*Streptococcus* mutant fructosyltransferase gene); Steinmetz et al. (1985) *Mol. Gen. Genet.* 20:220 (levansucrase gene); Pen et al. (1992) *Bio/Technology* 10:292 (α-amylase); Elliot et al. (1993) *Plant Molec. Biol.* 21:515 (tomato invertase genes); Sogaard et al. (1993) *J. Biol. Chem.* 268:22480 (barley α-amylase gene); and Fisher et al. (1993) *Plant Physiol.* 102:1045 (maize endosperm starch branching enzyme II)).

The following examples are provided to illustrate certain particular features and/or embodiments. The examples should not be construed to limit the disclosure to the particular features or embodiments exemplified.

EXAMPLES

Example 1

Determination of Total Oil Content in Bulk Soybean by Potassium Hydroxide Hydrolysis and a Coupled Enzyme Colorimetric Reaction The total oil content of ground soybeans was measured. Oil was solvent extracted from dried, ground soybeans, and saponified using potassium hydroxide. The glycerol produced was then measured colorimetrically using a coupled enzymatic detection reagent. The enzymatic detection reagent provided an absorbance maximum at 540 nm in the presence of glycerol, which was monitored with a spectrophotometer. The increase in absorbance at 540 nm was directly proportional to the glycerol concentration in the sample, and was used to calculate the total triglyceride (oil) content of the ground soybean samples. The amount of free glycerol already in the oil was found to be negligible.

Oil Extraction

Approximately 20 g of whole soybeans were weighed out into a small metal weigh pan. This sample was then placed in an oven for 2 hours at 60° C. to dry the sample. Then, the sample was moved into a desiccator until the sample was equilibrated to room temperature. After equilibration, the sample was ground with a Retsch Grindomix™ (mini robot coop) for 20 sec at 10,000 rpm. The ground sample was then transferred into a 1.5 oz snap-top container, and placed in the desiccator until use.

200 mg of ground sample was weighed into a 6.5 mL scintillation vial, and a BS-5 steel ball was added to the vial containing the sample. Then, 4 mL heptanes was added to the vial, and the vial was capped. The heptanes-containing sample vials were placed in a tube holder, and the tube holder was placed in a GenoGrinder (SPEX SamplePrep). The vial contents were homogenized at a setting of 200 for 4 minutes. After homogenization, the tube holder was placed in a Block Vortexer, and mixed for 5 minutes at a motor speed setting of 7.

Centrifuge for 5 minutes at 2500 rpm in a swinging bucket centrifuge.

Quantification

Preparation of curve, quality controls (QCs), and blank:

A series of standard oil concentrations from 10 mg/mL to 0.5 mg/mL (to construct a reference curve) was prepared in 6.5 mL scintillation vials, using 100 mg/mL stock standard of the oil to be tested: 10 mg/mL (500 μL of 100 mg/mL, diluted to 5.0 mL with heptanes); 8 mg/mL (400 μL of 100 mg/mL, diluted to 5.0 mL with heptanes); 6 mg/mL (300 μL of 100 mg/mL, diluted to 5.0 mL with heptanes); 4 mg/mL (200 μL of 100 mg/mL, diluted to 5.0 mL with heptanes); 2 mg/mL (100 μL of 100 mg/mL, diluted to 5.0 mL with heptanes); 1 mg/mL (50 μL of 100 mg/mL, diluted to 5.0 mL with heptanes); and 0.5 mg/mL (25 μL of 100 mg/mL, diluted to 5.0 mL with heptanes).

For the blank, 5 mL heptanes (only) was transferred into a well.

For the QCs, samples were prepared at the lower 25% of the standard curve, as well as a high at about 75% of the curve (2.5 and 7.5 mg/mL, respectively).

Using a NX-Span 8 liquid handler, 50 μL of each sample was transferred into a 96-well dilution plate by placing the scintillation vials into a 24-well plate as a holder. The blank, curve standards, and QCs were also pipetted into the plate. The samples were transferred with a dilution factor of 1:80 (This volume can be adjusted according to the dilution needed to get results within the standard curve). Duplicates of every sample and standard were analyzed to determine the standard deviation and coefficient of variation (CV) for each sample.

The heptanes were evaporated with nitrogen using a 96-well drying apparatus.

After the heptanes had evaporated completely, 300 μL 2M KOH in Methanol was added to each well using the NX-MC liquid handler.

The samples were capped and shaken in the block vortex plate for 5.0 minutes.

700 μL 2M Tris Buffer, pH 7.0, was added to each well using the NX-MC liquid handler. The samples were capped and vortexed at low to medium speed for 5.0 minutes.

Aliquots of 175 μL of the working reagent were added to a microtiter plate.

For each sample, 25 µL of the sample was added to the plate containing the working free glycerol reagent using the NX-MC liquid handler.

The contents of each well were mixed by aspirating and dispensing several times.

The wells were incubated for 10 minutes at 37° C.

The absorbance at 540 nm of the samples on a plate reader was determined if the 4/1 Glycerol working reagent was being used. The absorbance at 500 nm of the samples on the plate reader was determined if the Pointe Scientific reagent was being used.

The average absorbance was plotted against the standard concentration for each of the curve points, and the blank's absorbance was subtracted from the standards and sample points. FIG. 1.

The oil concentration in each sample was calculated by the following formula, where Abs=Absorbance. Table 1.

(Abs. Sample)/(Abs. Standard)×(Conc. Standard)=mg/dl (triolein)

Sample Calculation: If Abs. Sample=0.300, Abs. Standard=0.200, and Conc. of Standard=200 mg/dl: 0.300/0.200×200 mg/dl=300 mg/dl Triglycerides. (To obtain values in S.I. Units, multiply mg/dl×0.11=mmol/L).

understanding of how each sub-trait contributes to increased oil content in these inbreds. We have also identified the best inbred lines for QTL mapping of each important sub-trait, and discovered a corn line (SRS72NE) with much lower levels of saturated fatty acids than normal corn inbreds. Characterization of high-oil maize germplasm in the past has been limited to measuring whole kernel (seed) oil by NIR or NMR, which at least partially explains why these oil characteristics were not previously discovered (Channabasavaradhya et al., SAGE #2003385; Clayton et al., SAGE #100999).

Plant Materials

Ten kernels from each of the following inbreds were soaked in $H_2O$ overnight, dissected into embryos and endosperms (including aleurone and paricarp), and lyophilized overnight. Whole kernel weight was measured prior to dissection, and components were weighted after lyophilization.

The high oil lines analyzed (Pedigree relationship shown in FIG. 2) were: UUQ21-2 (C99 SibsBxHO/6UQ025); UUQ21-7 (C99 SibsBxHO/6UQ025); UUQ21-9 (C99 SibsBxHO/6UQ025); UTS51NE (4XZ756/UUQ21-9-1-1//MV8735); SRS57NE (7SH382/6UQ025//BE4207);

TABLE 1

Total oil content of bulk soybean samples

| Sample | Wells | Absorbance Values | Calculated Concentration (mg) | Average Concentration | Dilution | Average Total Oil per rep (mg) | Weight (mg) | Average Percent Oil per rep | Sample Average Percent Oil |
|---|---|---|---|---|---|---|---|---|---|
| 21 a-1 | A3 | 0.463 | 0.516 | 0.515 | 80 | 41.16 | 201.80 | 20.40 | 19.92 |
| 21 a-2 | A4 | 0.460 | 0.513 | | | | | | |
| 21 b-1 | B3 | 0.412 | 0.461 | 0.493 | 80 | 39.40 | 202.60 | 19.45 | |
| 21 b-2 | B4 | 0.470 | 0.524 | | | | | | |
| 22 a-1 | C3 | 0.437 | 0.488 | 0.497 | 80 | 39.72 | 204.40 | 19.43 | 19.32 |
| 22 a-2 | C4 | 0.453 | 0.505 | | | | | | |
| 22 b-1 | D3 | 0.417 | 0.466 | 0.479 | 80 | 38.28 | 199.40 | 19.20 | |
| 22 b-2 | D4 | 0.440 | 0.491 | | | | | | |
| 23 a-1 | E3 | 0.395 | 0.443 | 0.464 | 80 | 37.08 | 198.70 | 18.66 | 18.89 |
| 23 a-2 | E4 | 0.433 | 0.484 | | | | | | |
| 23 b-1 | F3 | 0.403 | 0.451 | 0.480 | 80 | 38.36 | 200.70 | 19.11 | |
| 23 b-2 | F4 | 0.456 | 0.508 | | | | | | |
| 24 a-1 | G3 | 0.414 | 0.463 | 0.487 | 80 | 38.92 | 202.10 | 19.26 | 19.08 |
| 24 a-2 | G4 | 0.457 | 0.510 | | | | | | |
| 24 b-1 | H3 | 0.420 | 0.470 | 0.478 | 80 | 38.24 | 202.20 | 18.91 | |
| 24 b-2 | H4 | 0.435 | 0.486 | | | | | | | a = duplicates from the same sample extraction tube
b = second extraction tube

Example 2

Oil Contents & Fatty Acid Profiles of High-Oil Maize Germplasm

Figure 2:
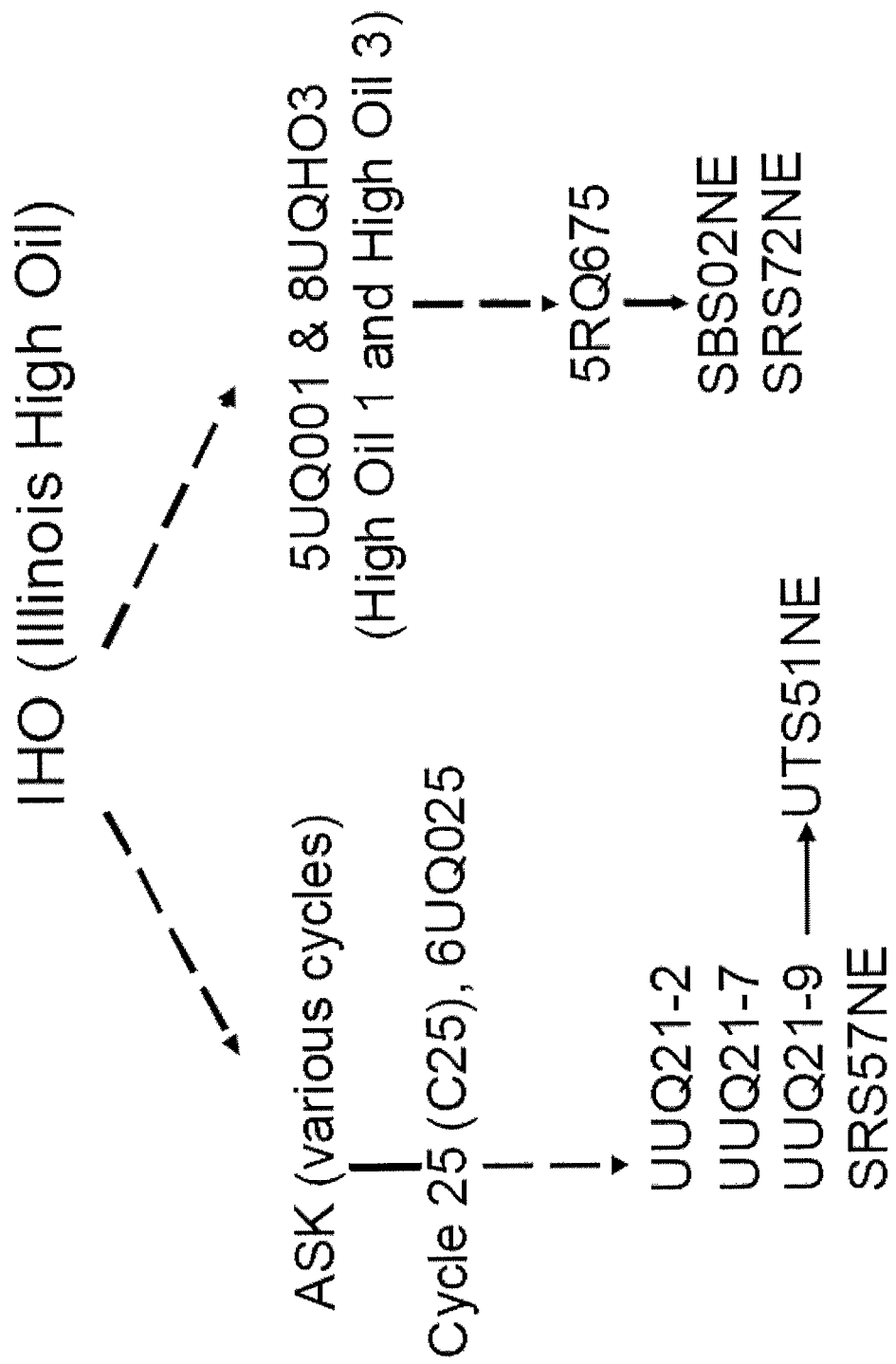
FIG. 2 includes an illustration of pedigree relationships of certain exemplary high-oil inbred corn varieties with IHO and ASK.

Corn oil is an important resource for direct human consumption, increasing bio-diesel production and livestock feed. Several important high-oil germplasms can be traced to IHO or ASK corn populations. FIG. 2. Through traditional breeding, a number of lines with high oil content, good general and specific combinabilities such as 5RQ675, UTS51NE and their derivatives have been developed and widely used in hybrid creation.

The objectives of this study were to determine oil contents, fatty acid profiles and oil related sub-traits such as embryo oil concentration, embryo size (endosperm/embryo ratio; EER) and endosperm oil of high oil germplasm in detail. As a result of this study, we have a much better 5RQ675 (2HOB0014.1B/FR1064//C S405); SB SO2NE (5RQ675/SLB01); SRS72NE (5RQ675/7RN401); 5UQ001; 8UQHO3; and 5RQ311 (HO4617/FR992-4 KPTYPE, oil checks).

The normal oil lines were: 7SH382; XHH13; 6RC172; and MV8735.

Total oil measurement: For total oil analysis, lyophilized materials were ground and extracted with heptanes, followed by potassium hydroxide hydrolysis (saponification) for total oil content measurement by absorbance. Briefly, heptanes-extracted triacylglycerols (TAGs) were hydrolyzed to glycerol and free fatty acids by 2M KOH. The glycerol was then measured by several additional coupled enzyme reactions. The end reaction showed an absorbance maximum at 540 nm, which was monitored with a spectrophotometer. The increase in absorbance at 540 nm is directly proportional to the glycerol concentration or total oil content in the samples.

Results and Discussion

Phenotypic Data

A total of 27 weight and oil related sub-traits were measured for eleven high-oil and four normal-oil inbreds and summarized in Table 2. More detailed analyses of important sub-traits are described below.

Some High-Oil Donors Have Increased Endosperm Oil

Figure 5:
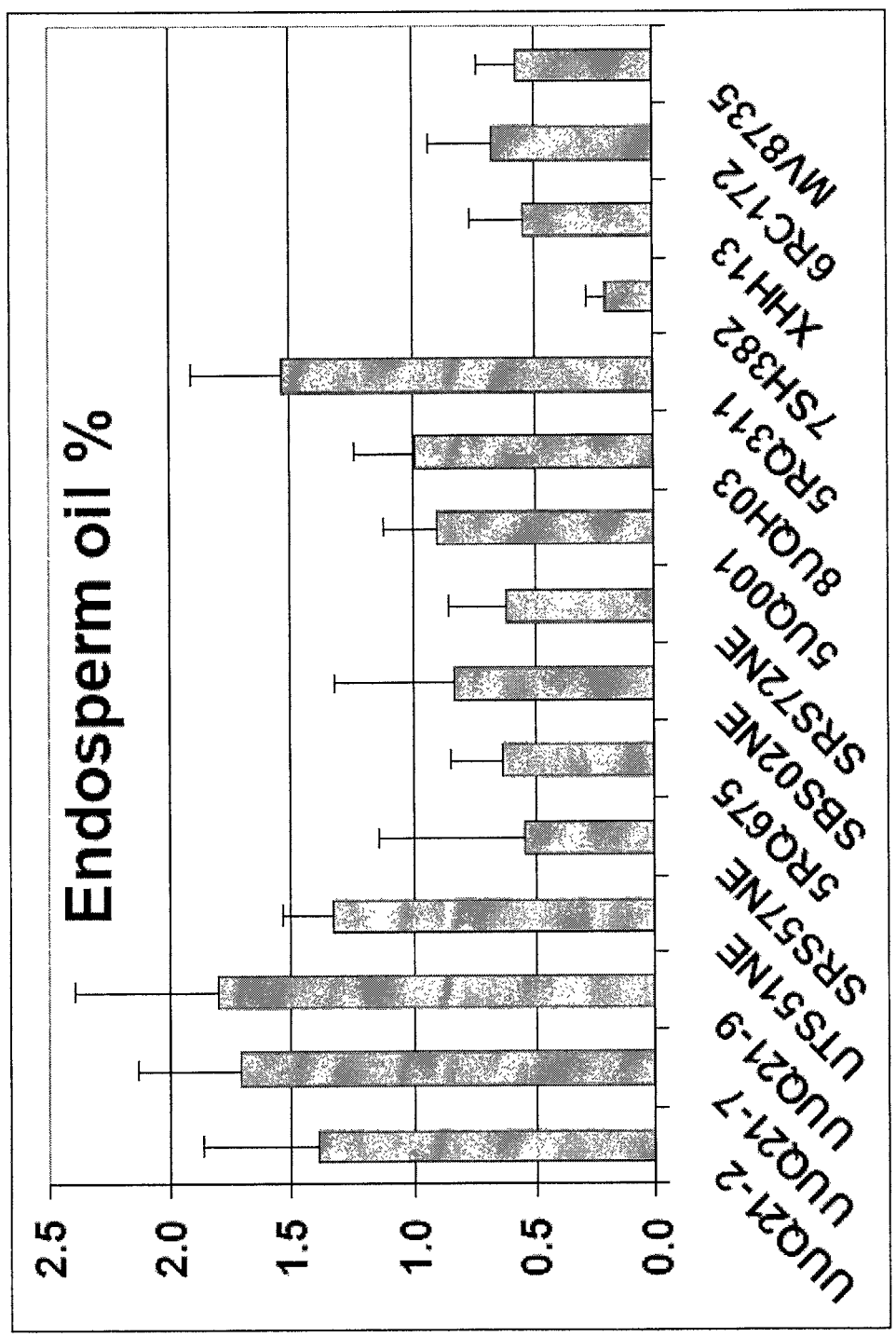
FIG. 5 includes a chart summary of the endosperm oil (%) data determined in several exemplary high-oil inbred corn varieties.
Figure 6:
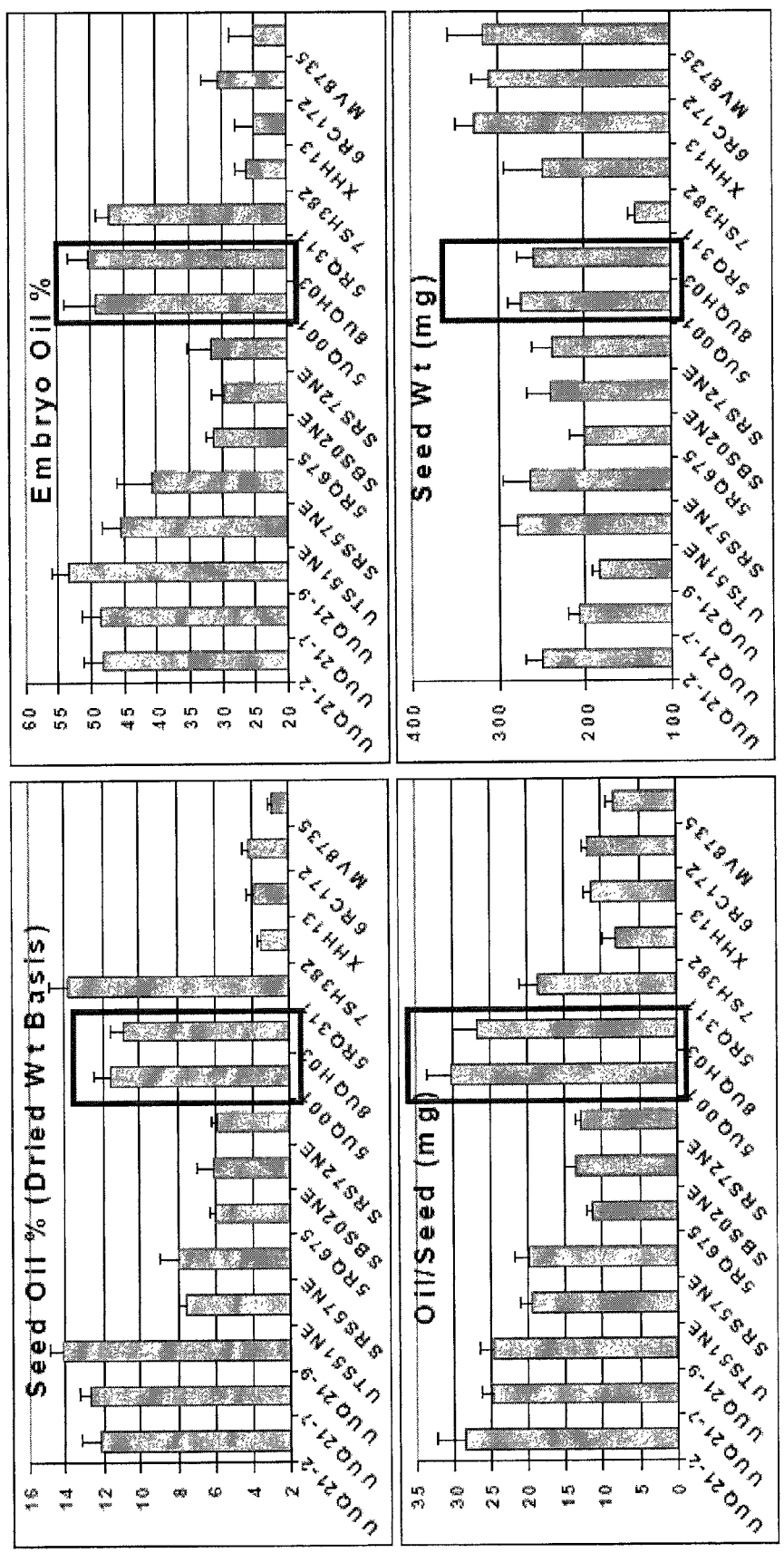
FIG. 6 includes a chart summary of oil characteristics of exemplary inbred corn varieties, 5UQ001 and 8UQHO3.

As expected, overall endosperm oil % (0.5 to 1.8%) is much lower than embryo oil %, as illustrated in FIG. 5. It was also determined that endosperm oil concentrations in some high-oil lines (UUQ21-7, UUQ21-9 and 5RQ311) are three times higher than those of the normal inbreds. 5RQ675

TABLE 2

Phenotypic data summary. Data are based on averages of 10 kernels or embryos for each inbred. EER = embryo/endosperm weight ratio. C12:0, C20:2, and C22:1 were not detectable. FAME data are for embryos only.

| Inbred | Seed wt. (mg) | Emb. wt. (mg) | Emb. oil (mg) | Emb. oil (%) | Endo. wt. (mg) | Endo. oil (mg) | Endo. oil (%) | Oil/seed (mg) | EER | Seed oil % (dried wt.) | Seed oil % (air dried) |
|---|---|---|---|---|---|---|---|---|---|---|---|
| UUQ21-2 | 249.4 | 53.8 | 26.0 | 48.3 | 181.9 | 2.5 | 1.4 | 28.5 | 3.4 | 12.1 | 11.4 |
| UUQ21-7 | 209.2 | 46.1 | 22.4 | 48.7 | 151.4 | 2.6 | 1.7 | 25.0 | 3.3 | 12.7 | 12.0 |
| UUQ21-9 | 183.1 | 41.7 | 22.3 | 53.6 | 133.0 | 2.4 | 1.8 | 24.7 | 3.2 | 14.2 | 13.5 |
| UTS51NE | 277.8 | 36.5 | 16.6 | 45.4 | 222.6 | 3.0 | 1.3 | 19.5 | 6.1 | 7.5 | 7.0 |
| SRS57NE | 263.8 | 46.4 | 18.6 | 40.7 | 202.8 | 1.2 | 0.5 | 19.8 | 4.4 | 8.0 | 7.6 |
| 5RQ675 | 201.4 | 33.6 | 10.5 | 31.3 | 156.9 | 1.0 | 0.6 | 11.5 | 4.7 | 6.0 | 5.7 |
| SBS02NE | 239.1 | 40.2 | 11.9 | 29.5 | 183.5 | 1.5 | 0.8 | 13.4 | 4.7 | 6.1 | 5.7 |
| SRS72NE | 237.6 | 37.5 | 11.7 | 31.7 | 184.2 | 1.1 | 0.6 | 12.8 | 5.0 | 5.8 | 5.4 |
| 5UQ001 | 274.1 | 57.6 | 28.4 | 49.4 | 203.7 | 1.8 | 0.9 | 30.2 | 3.5 | 11.6 | 11.0 |
| 8UQH03 | 261.2 | 49.6 | 25.0 | 50.4 | 198.7 | 2.0 | 1.0 | 27.0 | 4.0 | 10.8 | 10.3 |
| 5RQ311 | 140.0 | 36.3 | 17.0 | 47.0 | 96.8 | 1.5 | 1.5 | 18.5 | 2.7 | 13.8 | 13.1 |
| 7SH382 | 248.1 | 29.5 | 7.7 | 26.3 | 204.3 | 0.4 | 0.2 | 8.2 | 7.0 | 3.5 | 3.3 |
| XHH13 | 325.9 | 39.9 | 9.9 | 25.0 | 261.0 | 1.4 | 0.5 | 11.3 | 6.6 | 3.8 | 3.5 |
| 6RC172 | 309.5 | 33.7 | 10.2 | 30.5 | 253.2 | 1.6 | 0.7 | 11.9 | 7.6 | 4.1 | 3.8 |
| MV8735 | 315.8 | 27.3 | 6.7 | 25.1 | 263.7 | 1.5 | 0.6 | 8.2 | 9.8 | 2.8 | 2.6 |

Significant Variation in Whole-Seed Oil

Figure 3:
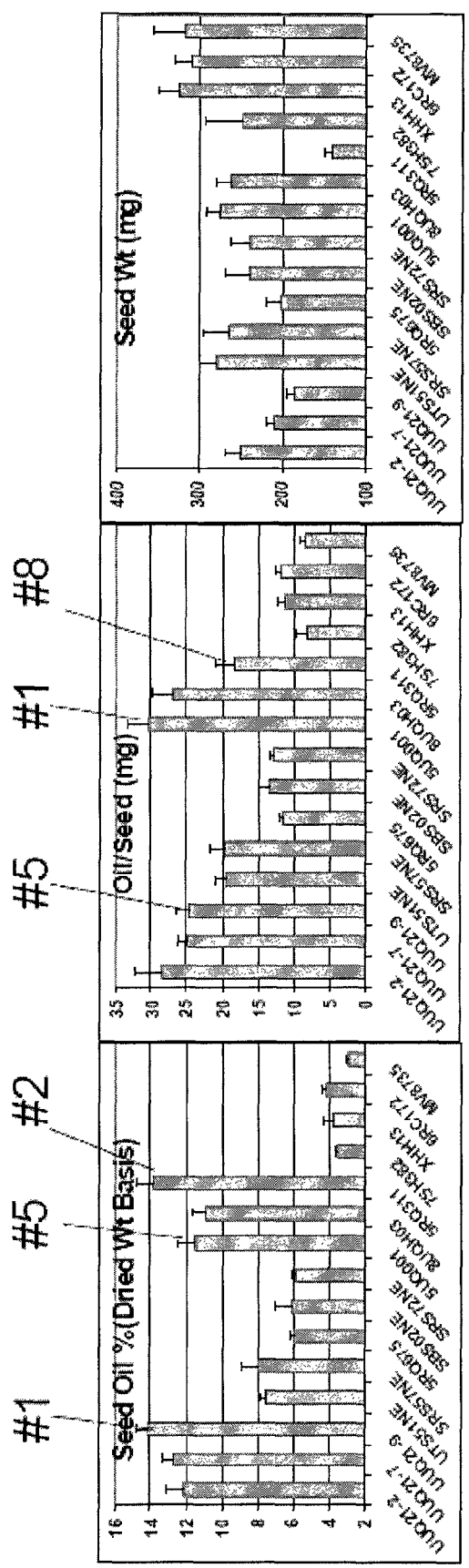
FIG. 3 includes a chart summary of the differences in whole seed oil determined in several exemplary high-oil inbred corn varieties. Hashmark numbers (#) indicate the relative ranking of the seed oil content (%) and oil/seed (mg) among eleven exemplary high-oil varieties. Error bars represent standard deviation.

Seed oil (%), oil/seed, and seed weight data are presented in FIG. 3. Note that the seed oil (dried wt basis, left panel) of eleven high-oil inbreds varies from around 5.8 to 14.2%, and all of them are significantly higher than those of the four normal inbred lines (which are less than 4.1%). When expressed in mg oil/seed (middle panel), most of high-oil lines have more oil than normal-oil lines, except 5RQ675 and its derivatives, SBSO2NE and SRS72NE. However, rankings of each high-oil inbred among the eleven change dramatically for some sub-traits. For example, UUQ21-9 ranks #1 in seed oil, but is #5 in oil/seed; 5UQ001 is number #5 in seed oil, but #1 in oil/seed; and 5RQ311 ranks #2 in seed oil, but only #8 in amount of oil per seed. The ranking discrepancy is largely due to the seed weight difference of each inbred, shown in the right panel. These data reinforce our notion that measuring seed oil (%) alone can be misleading in characterizing the seed oil characteristics of particular corn varieties.

Significant Variations in Embryo Oil Concentration & Embryo Size

Figure 4:
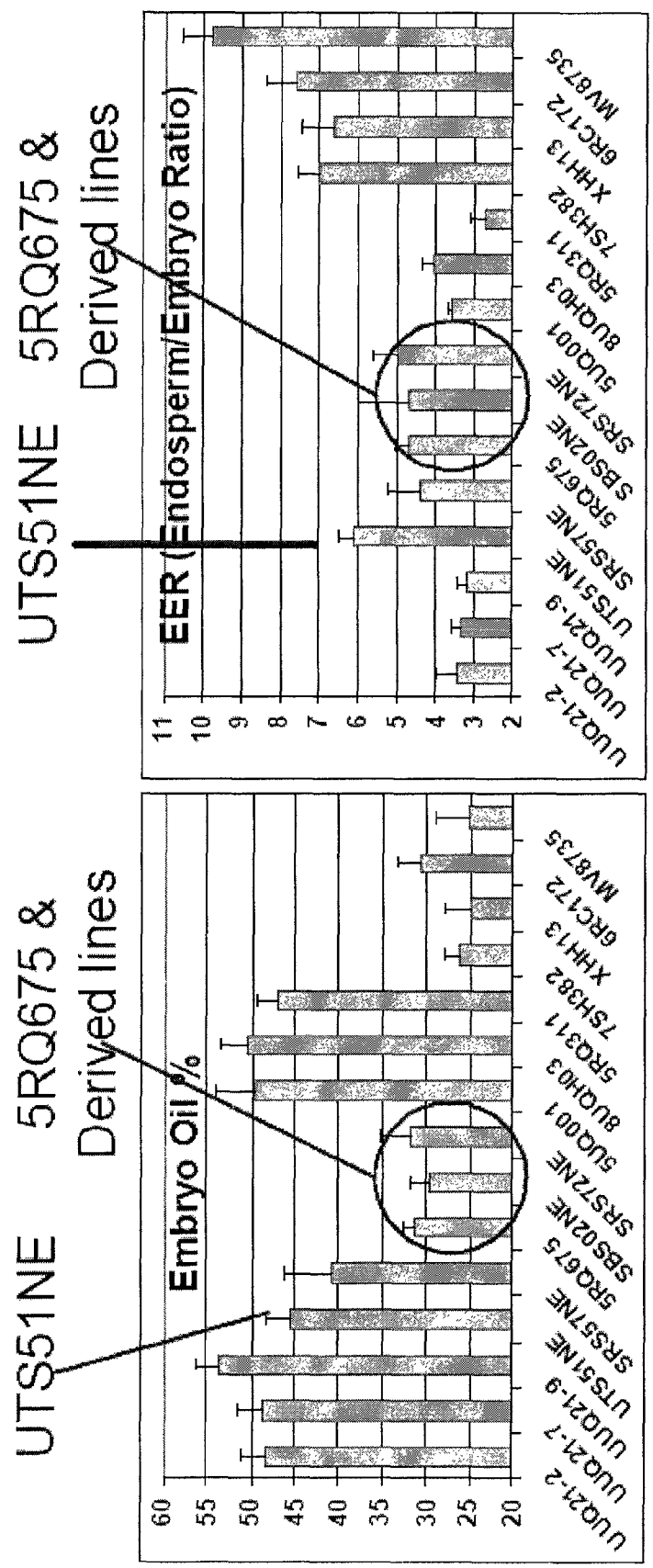
FIG. 4 includes a chart summary of the embryo oil (%) and EER data determined in several exemplary high-oil inbred corn varieties.

Variations in embryo oil (%) and endosperm/embryo ratios (EER, a good indication of embryo proportion of the seed) are shown in FIG. 4. The embryo oil of the eleven high-oil inbreds varies from about 29.5 to 53.6%, and EER varies from about 2.7 to 6.1%. Most of the high-oil inbreds have increased embryo oil concentration and increased embryo proportion (decreased EER). However, UTS51NE gets most of its oil increase from elevated embryo oil (%), and is a good donor for embryo oil concentration QTL mapping and gene discovery. On the other hand, 5RQ675 and its derivatives, SBSO2NE and SRS72NE, only have slightly elevated embryo oil (%), and appear to derive most of their oil increase from larger embryo proportion (smaller EER). These lines are good donors for embryo size, QTL mapping, and gene cloning.

and its derivative lines appear to have normal endosperm oil %. Interestingly, SRS57NE, which has a much elevated embryo oil % (40.7%) and a reduced EER (4.4), appears to have a relatively normal endosperm oil % (0.5%), suggesting that at least in some inbreds, increasing endosperm oil and embryo oil are achieved by different mechanisms.

Example 3

Phenotypic Analysis of Segregating Corn Kernels from a High Oil Content Donor

Segregating $F_2$ kernels from crosses between an oil donor corn line, 6UQ025, and three elite, normal oil parental lines were measured for kernel weight, total oil content per kernel, and kernel amylose content.

The high oil corn line, 6UQ025 (~18% oil content) was used as the first generation oil donor in a marker-assisted high oil corn conversion program. The first map indicated a major oil locus or segment marked by Phi61/Phi65 on Ch-9 (Ch9-45/55), which explained more than 50% of the observed oil variance. With one copy of the locus (or segment), it could elevate 1.4% oil content in allele substitution calculations. Unfortunately, this locus is very tightly linked to a waxy kernel phenotype, making the separation of these traits very difficult.

To support a nutritionally enhanced corn program, it was thus very important to have a solid understanding of the oil QTLs in 6UQ025, both in terms of gene-by-gene and gene-by-environment interactions. Additionally, it was important to explore how other kernel components affect oil composition. Previous studies that utilized bulk seed samples to determine the oil phenotype failed at separating the waxy kernel type from the oil trait. This study describes the efforts and results of phenotyping single $F_2$ kernels derived from crosses of normal elite corn inbreds and the waxy high oil donor line 6UQ025, in order to overcome this limitation of conventional techniques. Single kernel phenotyping could not be adequately achieved by such conventional techniques.

Analysis of Total Kernel Oil Content

Single seed analysis was used in $F_2$ seed to phenotype oil, seed weight, and amylose.

Oil Extraction. The single seeds were weighed to the nearest tenth of a milligram and placed into a 6.5 mL scintillation vial (Simport #4411). The samples were then individually crushed using an arbor press, followed by the addition of one 5/16 inch steel ball (catalog number BS-5, Small Parts Inc.) to each vial. The vials were then capped and dry ground in a GenoGrinder (SPEX SamplePrep) for 3 minutes at 750 strokes/minute. The samples were then vortexed and reground for 3 minutes at 750 strokes/minute. Hexane (4 mL) was then carefully added to the vials, which were recapped and placed back into the GenoGrinder for an additional 3 minutes, followed by a Troemner VX-2400 block vortex for 3 minutes at 8000 rpm. The vials were then centrifuged at 3000 rpm at 6° C. for 10 minutes in a Beckman Coulter J6-MI centrifuge.

Reagent Preparation. No Prep is needed for the Pointe Scientific Triglyceride Reagent (Pointe Scientific, Cat # T7532-120mL). For the Glycerol working reagent (Sigma), a 2M Tris buffer, pH 7.0, was prepared by dissolving 121.1 g Sigma 7-9 Tris (Sigma Cat # 1378) into 425 mL Milli-Q water with the aid of a stir bar. The buffered solution was adjusted to pH 7.0 with concentrated HCL. The volume was brought up to a final volume of 500 mL with Milli-Q water. A 2 M KOH in Methanol solution was prepared by dissolving 56.1 g KOH (Sigma Cat # P1767) pellets into 450 mL methanol with the aid of a stir bar, and bringing to a final volume of 500 mL with methanol.

Standard Curve Preparation. 100 mg/mL working oil standards were prepared by precisely weighing 1000 mg of a new refined vegetable seed oil into a 10 mL volumetric flask, and diluting the oil with heptanes up 10 mL. The standard curve was prepared following the subsequent Table 3 in labeled 6.5 mL scintillation vials.

QC standards were prepared by repeating the above procedure, using a secondary oil source.

TABLE 3

Standard curve generation

| Curve point | 100 mg/mL working oil | Heptanes |
| --- | --- | --- |
| 10 mg/mL | 500 μL | 4500 μL |
| 8 mg/mL | 400 μL | 4600 μL |
| 6 mg/mL | 300 μL | 4700 μL |
| 4 mg/mL | 200 μL | 4800 μL |
| 2 mg/mL | 100 μL | 4900 μL |
| 1 mg/mL | 50 μL | 4950 μL |
| 0.5 mg/mL | 25 μL | 4975 μL |
| Blank | 0 | 5000 μL |
| QC 2 mg/mL | 100 μL* | 4900 μL |
| QC 8 mg/mL | 400 μL* | 4600 μL |

*Secondary oil source

Quantification 100 uL of each of the standard curve points, blank, QCs, and extracted oil samples were transferred to a 96-well extraction plate. A robot, (e.g., a NX-span-8 Beckman Coulter) can be used for this transfer. This standard curve was designed to target a single seed total percent oil in the range of 3-7%.

Once the samples have been aliquoted into the 96-well extraction plate, the heptanes was dried off under a constant stream of nitrogen at 60° C., followed by the addition of 300 μL 2M KOH in Methanol. The plate was then capped and vortexed for 5.0 minutes at 4000 rpm on a block vortex. The caps were then removed, and 700 μL 2 M TRIS Buffer, pH 7.0, was added to the wells.

The plate was recapped and vortexed gently for 5.0 minutes at 2000 rpm on a block vortex. 25 μL of each sample is then transferred to a 96-well spectrophotometer plate containing 175 μL of the Triglyceride reagent from Pointe Scientific. The sample was mixed by pipetting up and down in the tip several times. Once the samples were properly mixed, the spectrophotometer plate was placed, uncovered, in a oven at 37° C. for 10 minutes, followed by reading the plate on a spectrophotometer set at 500 nm. The entire foregoing process can be performed on a multi-channel robot for automation.

The curve points were plotted using the plate reader's SoftMax™ software, with the blanks being subtracted out of all standards and unknowns. The standard curve had an $R^2$ of greater than 0.99 before the unknowns were quantified. The QC calculated concentrations were checked for agreement with the known amounts. Coefficients of variation (CVs) were calculated for each replicate of the unknowns. Any with a CV greater than 15% were thrown out and rerun. The concentration data obtained was exported to Excel, and the percent oil per kernel was calculated using the weights that were recorded at the start of the assay.

Analysis of Kernel Amylose Content

The amylose content in defatted corn meal from single kernels was measured using a colorimetric method. A 30 mg sample of defatted corn flour was weighed into a 16×100 mm screw cap test tube and mixed with 3 mL 9:1 dimethyl sulfoxide:water containing 60 mM iodine. The tubes were tightly capped and heated in a boiling water bath for one hour, with vortexing every 15 minutes. The tubes were cooled to room temperature, and aliquots were diluted 1:200 with deionized water. After thirty minutes incubation at room temperature, the absorbance at 600 nm was measured. The amylose content was determined by comparison with a standard curve constructed from mixtures of standard amylose (70% high amylose from corn) and amylopectin (from waxy corn) in different ratios between 0 and 70%. A linear absorbance response was obtained for amylose (%) over the range tested ($r^2$=0.999).

Analysis of Results

The analytical data for single seeds was analyzed using the JMP™ software program. Waxy kernel types were identified as any kernel having an amylose content of ≤5%. Data for parent lines, and segregating progeny, were compared using a one-way analysis of variance to show the means and distribution of data from kernels classified as waxy or normal based on the amylose content. To verify the pattern of results, the same analysis was performed breaking the data out by location to determine if similar results were obtained between environments.

Results

One of the primary goals of this study was to provide phenotypic characterization of a segregating population in order to support a genetic mapping study. In the population under study, identifying genetic markers for the high kernel oil content trait and clearly distinguishing them from the closely associated waxy kernel type of the donor line was necessary. By using single kernel phenotyping techniques, it was possible to identify segregation among the kernels for the low amylose, high oil, and kernel weight characteristics. The results of the individual analyses are discussed below.

Amylose Content

The means and ranges of the kernel amylose content (% amylose per kernel) for either parent types or segregating kernels were measured. A kernel was designated as "waxy" if it had an amylose content of ≤5% of the kernel mass. Although the 6UQ025 donor was typically <4% amylose, and the elite parents were >12% amylose, the $F_2$ progeny showed a much wider range of segregation for amylase content, with maximum contents greatly exceeding that of the elite parent. This was interesting in that the waxy trait is corn is known to be a simply inherited trait. This wide range of kernel amylose content suggested a more complicated inheritance pattern, and possibly multiple genes being involved in this trait. The classification between identifying a kernel as waxy (≤5% amylose) and non-waxy (>5% amylose) is somewhat arbitrary, as a few kernels identified as "normal" have amylose contents only slightly above the 5% cut-off value. The 6UQ025 donor line had a maximum amylose content of 3.3%, so the 5% value was taken as a conservative cut-off point. For each of the three crosses, 90% of the waxy kernels had amylose contents of <4%.

Kernel Mass

Another variable in the cross between the 6UQ025 donor and the three elite parent lines was the disparity in kernel mass. The elite parents each had a median kernel mass of >250 mg, while the 6UQ025 had a median kernel mass of <200 mg. Since kernel mass is a factor in calculating the ratio of kernel oil to kernel mass, or percent oil content, it was important to understand the variability in kernel mass.

The means and ranges of kernel mass for the parent lines and $F_2$ progeny from each of the three crosses were measured. In all cases, the $F_2$ progeny had an average kernel mass higher than the 6UQ025 oil donor parent. The $F_2$ normal kernels had a slightly higher kernel mass than the $F_2$ waxy kernels. For all $F_2$ progeny, the range of kernel mass was greater than that measured for the parent lines.

Total Kernel Oil Content

To avoid the confounding of kernel oil content with kernel mass, the total oil content on a per kernel basis was measured. The means and range of oil contents for the parent lines and the segregating $F_2$ progeny were grouped on the basis of waxy or normal amylose contents. The elite parent lines had a relatively narrow distribution of total kernel oil contents, with median oil contents of 8-11 mg/kernel. The 6UQ025 oil donor line had a median oil content of 24.1 mg/kernel, over twice the value for the normal parent lines. The $F_2$ progeny from the three crosses showed a wide range of oil contents, ranging from the normal parent values to higher than the oil donor parent. In all cases, the oil contents of waxy $F_2$ progeny were slightly higher than the non-waxy progeny. The $F_2$ mean kernel oil contents were all significantly elevated above the elite parent lines. The high oil contents of the non-waxy $F_2$ kernels indicate the high oil trait was successfully separated from the waxy kernel type in these progeny. Interestingly, progeny derived from the cross of V72 with 6UQ025 had the highest oil content per kernel of the three crosses, suggesting some additional factors influencing oil content in the V72 parent line.

Percent Oil Content

The ranges of percent oil contents in the parent lines and $F_2$ progeny from the crosses were measured. The 6UQ025 had the highest percent oil content, due to the higher oil per kernel content and the lower kernel mass. The trend for higher percent oil in the waxy kernel $F_2$ progeny relative to the non-waxy progeny is apparent for similar reasons. The V72 population again showed a higher overall level of percent oil content than the other two crosses.

Relationship Between Oil Content and Kernel Mass

The relationship between kernel oil content and kernel mass for the parent lines and the $F_2$ progeny were measured. Of the three populations, there appeared to be a weaker relationship between oil content and kernel mass for the 6RC172 population. In contrast, there was a much stronger relationship between total oil content and kernel mass when 7SH382 was the elite parent.

Relationship Between Oil and Amylose Contents

The relationship between kernel oil content and amylose content (%) was measured for the non-waxy $F_2$ progeny. There was a weak but significant negative relationship between kernel oil content and percent amylose content for progeny from all three crosses. No clear relationship existed in the waxy progeny, likely due to the narrow range of amylose contents (0-5%). Likewise, no clear pattern could be shown in the parent lines.

The foregoing analyses showed that the high oil content from the donor line could be separated from the waxy kernel type (low amylose content) of the same line. The single kernel phenotyping method was found to be capable of differentiating the progeny from three crosses. Previous efforts to separate the waxy kernel type from the high-oil characteristic met with limited success as bulk samples were analyzed and not single kernels.

On average, segregating kernels with a waxy kernel type were found to have higher percent oil contents than non-waxy high oil content segregates. When expressed on a total oil per kernel basis, the difference was less pronounced. Non-waxy type kernels had higher kernel weight than waxy type kernels. The $F_2$ segregation for amylose content was much wider than the range for either parent type, suggesting a less clear-cut distinction between the waxy and non-waxy kernel trait. There were slight negative correlations between total kernel oil content and amylose content in segregating kernels that were not considered waxy (% amylose ≤5%). These results show that single kernel analysis for amylose, kernel weight, and total oil was effective in identifying the separation of the waxy trait from the high oil trait that originated from the high oil donor.

Using single kernel analysis it was possible to accurately track each of the traits involved and co-segregating in the progeny: amylose content (waxy), oil content, and kernel mass. This phenotyping data can be used for genotyping efforts to identify markers associated with the high oil trait without confounding contributions from the other two related characteristics. Measuring the total oil per kernel also allowed separation of variation in kernel mass from variation kernel oil content, which variabilities are confounded when the percent oil content is measured.

TABLE 4

| | | | Defatted meal | | | | | | |
|---|---|---|---|---|---|---|---|---|---|
| Lab ID | Sample | Wells | Absorbance | Concentration | Dilution | Total Oil (mg) | weight (mg) | % Oil | Avg % Oil |
| Defatted Meal-1 | 1A | C3 | 0.042 | 0.036 | 80 | 2.88 | 228.2 | 1.26 | 1.35 |
| | 1B | C4 | 0.046 | 0.041 | 80 | 3.28 | 228.2 | 1.44 | |

TABLE 4-continued

| | | | | | | Total Oil | weight | | Avg % |
| Lab ID | Sample | Wells | Absorbance | Concentration | Dilution | (mg) | (mg) | % Oil | Oil |
| --- | --- | --- | --- | --- | --- | --- | --- | --- | --- |
| Defatted Meal-2 | 2A | D3 | 0.034 | 0.028 | 80 | 2.24 | 210.9 | 1.06 | 1.01 |
| | 2B | D4 | 0.031 | 0.025 | 80 | 2.00 | 210.9 | 0.95 | |
| Defatted Meal-3 | 3A | E3 | 0.027 | 0.021 | 80 | 1.68 | 203.0 | 0.83 | 0.79 |
| | 3B | E4 | 0.025 | 0.019 | 80 | 1.52 | 203.0 | 0.75 | |
| Defatted Meal-4 | 4A | F3 | 0.045 | 0.040 | 80 | 3.20 | 190.2 | 1.68 | 1.66 |
| | 4B | F4 | 0.044 | 0.039 | 80 | 3.12 | 190.2 | 1.64 | |

What is claimed is:

1. A method for identifying a plant comprising at least one oil trait or sub-trait, the method comprising:
    (a) providing a dried and ground sample of a plant material;
    (b) extracting oil from the dried and ground sample of the plant material;
    (c) admixing the extracted oil with a base, so as to saponify esters in the extracted oil and thereby produce glycerol;
    (d) reacting the glycerol with an enzymatic glycerol detection reagent to stoichiometrically convert the glycerol to a colored reaction product;
    (e) colorimetric analyzing the color reaction product to determine an amount of the glycerol in the sample and consequently an amount of oil in the plant material;
performing the steps (a) to (e) where the dried and ground sample is taken from a plant having a trait of high-oil content, to determine an amount of oil in the plant having a trait of high-oil content;
performing the steps (a) to (e) where the dried and ground sample is taken from a plant having a trait of normal-oil content, to determine an amount of oil in the plant having a trait of normal-oil content;
performing the steps (a) to (e) where the dried and ground sample is taken from a plant of interest, to determine an amount of oil in the plant of interest; and
    comparing the amount of oil in the plant of interest with the amount of oil in the plant having a trait of high-oil content and the amount of oil in the plant having a trait of normal-oil content to determine whether the plant of interest comprises the trait of high-oil content or normal-oil content.

2. The method according to claim 1, wherein the plant material is seed and the sample is an individual seed.

3. The method according to claim 1, wherein the plant material is seed and the sample is an individual seed embryo.

4. The method according to claim 1, wherein the plant material is obtained from a plant selected from a group consisting of corn, soya, canola, sunflower, and cotton.

5. The method according to claim 1, wherein the plant material is selected from a group consisting of vegetative plant material, seed, leaves, and roots.

6. The method according to claim 5, wherein the plant material is seed.

7. The method according to claim 6, wherein the plant material is an embryo.

8. The method according to claim 7, wherein the sample is a single plant seed embryo.

9. The method according to claim 1, wherein the sample is too small to provide accurate determination of the total oil content in the plant material by a method selected from the group consisting of gravimetric extraction of oil by an organic solvent and pulsed nuclear magnetic resonance (NMR) spectroscopy.

10. The method according to claim 1, wherein the sample is lyophilized.

11. The method according to claim 1, wherein extracting oil from the dried and ground sample of the plant material comprises extracting the oil from the sample using heptane as a solvent.

12. The method according to claim 1, wherein the base is an alkaline metal salt.

13. The method according to claim 12, wherein the base is KOH or NaOH.

14. The method according to claim 1, wherein colorimetric analyzing the color reaction product to determine the amount of glycerol in the sample comprises comparing data obtained with the sample and data obtained with an oil standard having a known oil content.

15. The method according to claim 14, wherein the oil standard having a known oil content is a refined, bleached, and deodorized oil standard.

* * * * *